US012758227B2

(12) United States Patent
Ashby et al.

(10) Patent No.: US 12,758,227 B2
(45) Date of Patent: Oct. 13, 2026

(54) SYSTEMS AND METHODS FOR ELECTRICALLY CHARGING INTERVENTIONAL DEVICES EX VIVO

(71) Applicant: Covidien LP, Mansfield, MA (US)

(72) Inventors: Mark P. Ashby, Laguna Niguel, CA (US); Bala Subramanya Pavan Kumar Kandala, Irvine, CA (US); Varun Umesh Kashyap, Irvine, CA (US); Kevin V. Nguyen, Westminster, CA (US); Ravi Sadasivuni, Aliso Viejo, CA (US)

(73) Assignee: Covidien LP, Mansfield, MA (US)

( * ) Notice: Subject to any disclaimer, the term of this patent is extended or adjusted under 35 U.S.C. 154(b) by 179 days.

(21) Appl. No.: 18/771,559

(22) Filed: Jul. 12, 2024

(65) Prior Publication Data

US 2025/0017588 A1 Jan. 16, 2025

Related U.S. Application Data

(60) Provisional application No. 63/513,157, filed on Jul. 12, 2023.

(51) Int. Cl.
*A61B 17/12* (2006.01)
*A61B 17/00* (2006.01)

(52) U.S. Cl.
CPC .. *A61B 17/12113* (2013.01); *A61B 17/12031* (2013.01); *A61B 17/12177* (2013.01); *A61B 2017/00017* (2013.01); *A61B 2017/00929* (2013.01); *A61B 2017/1205* (2013.01)

(58) Field of Classification Search
CPC ........ A61B 17/12113; A61B 17/12031; A61B 17/12177; A61B 2017/00017; A61B 2017/00929; A61B 2017/1205; A61B 2017/00526; A61B 2017/00884
See application file for complete search history.

(56) References Cited

U.S. PATENT DOCUMENTS

| | | | | |
|---|---|---|---|---|
| 11,471,163 | B2 | 10/2022 | Connor | |
| 2002/0120297 | A1 | 8/2002 | Shadduck | |
| 2017/0265870 | A1 * | 9/2017 | Kealey | A61F 2/856 |
| 2024/0225659 | A1 * | 7/2024 | Song | A61L 29/14 |

FOREIGN PATENT DOCUMENTS

| | | | |
|---|---|---|---|
| WO | 2017096188 | A1 | 6/2017 |

* cited by examiner

*Primary Examiner* — Paula J Stice
(74) *Attorney, Agent, or Firm* — Fortem IP LLP

(57) ABSTRACT

Medical systems for depositing fibrin on a medical device ex vivo are disclosed herein. According to some embodiments, the present technology includes a medical system comprising a vascular implant and a package defining a reservoir configured to receive the vascular implant and a volume of blood. The package can include an electrode disposed within the reservoir. The medical system can further include a current generator configured to be electrically coupled to the electrode. Activation of the current generator while the vascular implant and blood are present in the reservoir can cause current to flow through the blood and vascular implant, thereby applying an electrical charge to the vascular implant.

20 Claims, 8 Drawing Sheets

SYSTEMS AND METHODS FOR ELECTRICALLY CHARGING INTERVENTIONAL DEVICES EX VIVO

CROSS-REFERENCE TO RELATED APPLICATION(S)

The present application claims the benefit of priority to U.S. Provisional Patent Application No. 63/513,157, filed Jul. 12, 2024, which is incorporated by reference herein in its entirety.

TECHNICAL FIELD

The present technology relates to systems and methods for electrically charging interventional medical devices ex vivo.

BACKGROUND

Intracranial saccular aneurysms occur in 1% to 2% of the general population and account for approximately 80% to 85% of non-traumatic subarachnoid hemorrhages. Recent studies show a case fatality rate of 8.3% to 66.7% in patients with subarachnoid hemorrhage. Intrasaccular treatments of such intracranial aneurysms include braided and non-braided intrasaccular devices. These implants help occlude the aneurysm by disrupting the flow into the aneurysm, creating stagnation of blood in the aneurysm and eventually causing thrombus/occlusion in the aneurysm. Occlusion of the aneurysm using such devices depends on metal coverage at the neck and stability within the aneurysm sac. Although these implant methods have proven to have occlusion, adequate occlusion may take 6-12 months. As such, improved methods for occluding aneurysms are needed.

SUMMARY

The present technology relates to systems and methods for electrically charging interventional medical devices ex vivo. In particular embodiments, the present technology relates to novel packaging for electrically charging an intravascular implant ex vivo, in the presence of blood, to deposit fibrin on the implant prior to implantation. When the implant is implanted at a treatment site within a blood vessel (for example, within an aneurysm), the fibrin formed on the surface may accelerate occlusion within the aneurysm sac and lead to shorter healing times. Fibrin has also been shown to be a suitable matrix for Endothelial Progenitor Cell (EPC) growth, which may encourage more rapid endothelialization of fibrin-coated implant surfaces spanning the aneurysm neck and exposed to blood flow, which may reduce or eliminate the amount of time that the patient is on dual or single antiplatelet therapy. The subject technology is illustrated, for example, according to various aspects described below, including with reference to FIGS. 1-10. Various examples of aspects of the subject technology are described as numbered examples (1, 2, 3, etc.) for convenience. These are provided as examples and do not limit the subject technology.

1. A medical system, comprising:

a vascular implant;

a container configured to receive and secure the vascular implant thereto, wherein a portion of the container defines a reservoir configured to receive the vascular implant and a volume of blood, and wherein the container comprises a current generator and an electrode disposed within the reservoir and configured to be electrically coupled to the generator, wherein activation of the current generator while the vascular implant and blood are present in the reservoir causes current to flow through the blood and vascular implant, thereby applying an electrical charge to the vascular implant.

2. The medical system of Example 1, wherein the container is a first container and the medical system further comprises a second container configured to receive the first container therein while the vascular implant is secured to the first container.

3. The medical system of Example 2, wherein the second container is a sterile barrier.

4. The medical system of Example 2, wherein the vascular implant and first container are sterile prior to removal of the second container.

5. The medical system of any one of Examples 1 to 4, further comprising a tube extending from and in fluid communication with the reservoir, wherein the tube is configured to receive blood therethrough and deliver the blood to the reservoir.

6. The medical system of any one of Examples 1 to 5, wherein the current generator includes a power source configured to be in electrical communication with the electrode in the reservoir.

7. The medical system of any one of Examples 1 to 6, wherein the current generator includes a negative electrical terminal and a positive electrical terminal, and wherein the negative electrical terminal is configured to be in electrical communication with the electrode.

8. The medical system of any one of Examples 1 to 7, wherein the current generator includes a negative electrical terminal and a positive electrical terminal, and wherein the positive electrical terminal is configured to be in electrical communication with the vascular implant such that upon activation of the current generator, the container applies a positive charge to the vascular implant.

9. The medical system of any one of Examples 1 to 8, further comprising an introducer sheath detachably secured to the container.

10. The medical system of any one of Examples 1 to 9, further comprising a delivery member detachably coupled to the vascular implant, wherein the container includes a port at the sidewall of the reservoir, and wherein the delivery member is configured to extend from an interior portion of the reservoir through the port to a portion of the container outside of the reservoir.

11. The medical system of any one of Examples 1 to 10, further comprising an introducer sheath having a first end detachably coupled to the port and a second end, and wherein the delivery member is configured to extend through the port and into the introducer sheath.

12. The medical system of any one of Examples 1 to 11, further comprising a mask positioned over a portion of the vascular implant, thereby reducing and/or preventing the blood in the reservoir from contacting the portion of the implant.

13. The medical system of Example 12, wherein all or a portion of the mask is conductive.

14. The medical system of Example 12 or Example 13, wherein all of a portion of the mask is insulated.

15. A medical system, comprising:

a vascular implant;

a package defining a reservoir configured to receive the vascular implant and a volume of blood, the package including an electrode disposed within the reservoir; and a current generator configured to be electrically coupled to the electrode, wherein activation of the current generator while the vascular implant and blood are present in the reservoir causes current to flow through the blood and vascular implant, thereby applying an electrical charge to the vascular implant.

16. A method, comprising:

positioning a vascular implant in a reservoir;

while the vascular implant is positioned in the reservoir, exposing the vascular implant to blood contained within the reservoir; and while the vascular implant is exposed to the blood, delivering an electrical current to the vascular implant, thereby depositing fibrin onto the vascular implant.

17. The method of Example 16, wherein delivering the electrical current comprises positively charging the vascular implant.

18. The method of Example 16 or Example 17, wherein all of the vascular implant is exposed to the blood during delivery of the electrical current.

19. The method of Example 18, wherein the vascular implant is configured to be implanted within an aneurysm such that a first portion of the vascular implant is positioned over the neck of the aneurysm and a second portion of the vascular implant is configured to be positioned within the aneurysm sac.

20. The method of any one of Examples 16 to 19, wherein only a portion of the vascular implant is exposed to the blood during delivery of the electrical current.

21. The method of any one of Examples 16 to 20, wherein a first portion of the vascular implant is exposed to the blood during delivery of the electrical current and a second portion of the vascular implant is covered from the blood during delivery of the electrical current, thereby concentrating the electrical current at the first portion.

22. The method of Example 21, wherein the vascular implant is configured to be implanted within an aneurysm such that the first portion of the vascular implant is positioned over the neck of the aneurysm and the second portion of the vascular implant is configured to be positioned within the aneurysm sac.

23. The method of Example 21, wherein more fibrin is deposited at the first portion of the vascular implant during delivery of the electrical current than at the second portion.

24. The method of any one of Examples 16 to 23, further comprising sheathing the vascular implant within a tubular shaft after the deposition of fibrin on the vascular implant.

25 The method of any one of Examples 16 to 24, wherein the vascular implant is in electrical communication with a positive electrical terminal during delivery of the electrical current.

26. The method of any one of Examples 16 to 25, wherein the vascular implant is configured to be implanted in a patient, and wherein the blood is sourced from the patient.

27. The method of any one of Examples 16 to 26, further comprising implanting the vascular implant within a patient.

28 The method of Example 27, wherein the vascular implant is a stent or flow diverter.

29. The method of Example 27 or Example 28, wherein the blood is obtained from the side port of a vascular access sheath through which an interventional procedure is being performed on the patient.

30. The method of Example 29, wherein a syringe is used to obtain the blood from the side port of the vascular access sheath.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology provides devices, systems, and methods for electrically charging an interventional medical device ex vivo. Although many of the embodiments are described below with respect to devices, systems, and methods for intrasaccular occlusion of a cerebral or intracranial embolism, other applications and other embodiments in addition to those described herein are within the scope of the technology. For example, the medical systems disclosed herein can be used with embolization devices deployed outside of the neurovasculature, such as embolic devices used within the peripheral vasculature. In addition, the medical systems disclosed herein can be used with interventional devices configured for placement in a blood vessel, such as flow diverters and aneurysm bridging stents, and for treating vascular disorders other than aneurysms, such as arteriovenous malformations (AVM), vessel sacrifice, thrombectomy devices for treating ischemic stroke and stents for treating vessel stenosis.

Intrasaccular treatment of intracranial aneurysms includes devices placed in the aneurysm sac that occlude the aneurysm by disrupting the flow of blood into the aneurysm. This disruption of flow creates stagnation of blood in the aneurysm sac and eventually causes thrombus formation (and thus occlusion). While existing methods initially provide some occlusion, it may take 6-12 months to achieve a degree of occlusion that allows the aneurysm to permanently heal. As detailed herein, the medical systems of the present technology are configured to deposit fibrin on the surface of an interventional device (such as an intrasaccular implant) ex vivo, thereby shortening the time required for occluding the aneurysm and providing a more robust and stable therapeutic result.

Figure 1:
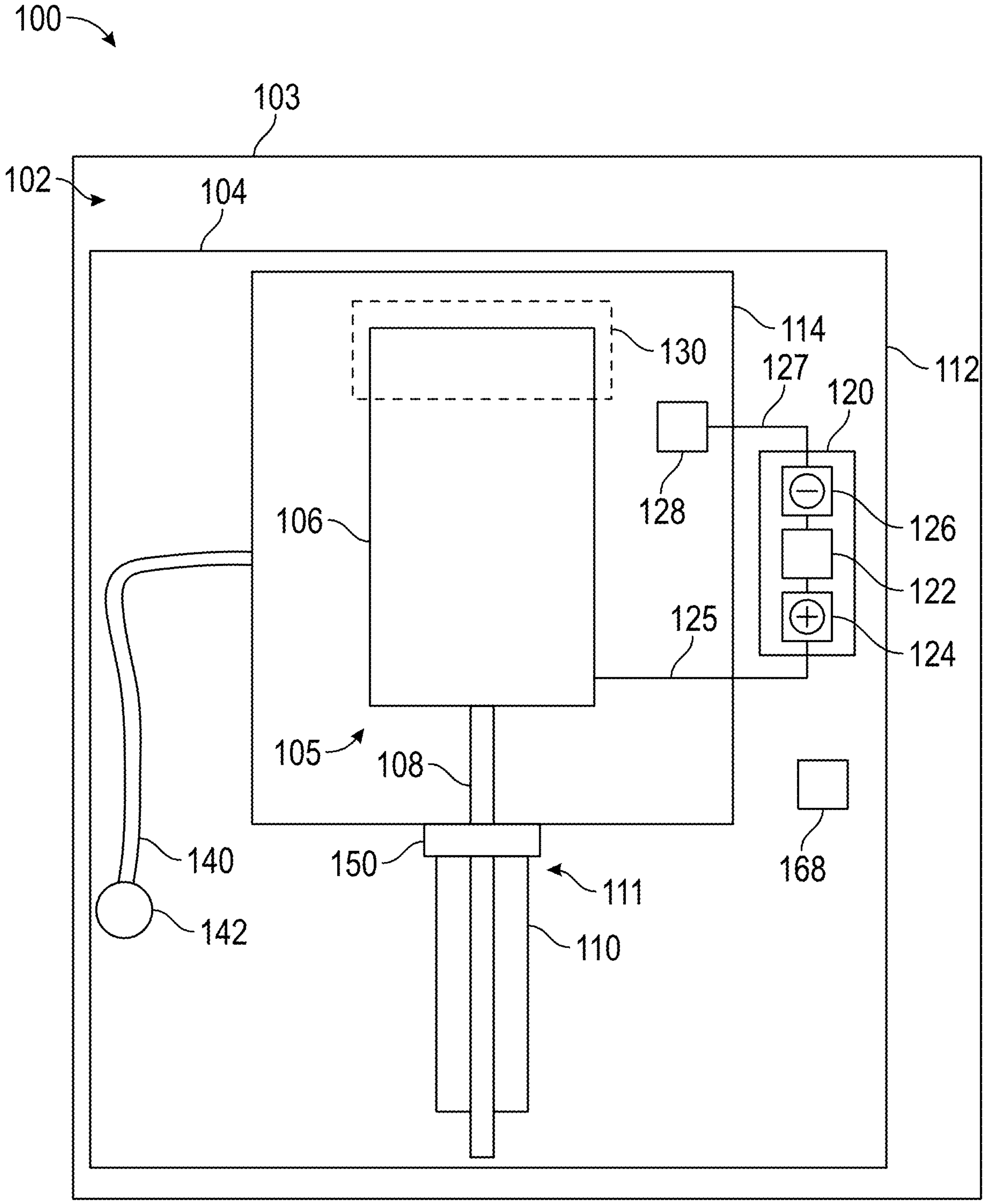
FIG. 1 schematically depicts a medical system configured in accordance with several embodiments of the present technology.

FIG. 1 schematically depicts a medical system 100 according to one or more embodiments of the present technology. The medical system 100 can comprise a packaging system 102 and a treatment assembly 105 including an interventional element 106 disposed in a reservoir 114 defined by a portion of the packaging system 102. The interventional element 106 can be configured to be implanted within the vasculature (such as an aneurysm) to treat one or more vascular defects. As detailed herein, the packaging system 102 can be configured to receive blood (such as the patient's blood) within the reservoir 114 such that the blood contacts exposed portions of the interventional element 106. The packaging system 102 can further be configured to provide an electrically charged environment within the reservoir 114 to encourage the formation of fibrin (recruited from fibrinogen in the blood) on the surface of the exposed portions of the interventional element 106.

In some embodiments, the interventional element 106 comprises an expandable mesh structure configured to be implanted within an aneurysm (such as an intracranial aneurysm) to occlude the aneurysm by disrupting the flow of blood from the parent vessel into the aneurysm. The treatment assembly 105 can further include a delivery member 108 having a proximal end configured to be manipulated by a user from an extracorporeal position, and a distal end detachably coupled to the mesh structure. The interventional element 106 is configured to be compressed into a low-profile state for advancement (along with the delivery member 108) distally through a delivery catheter (e.g., a microcatheter or other catheter, etc.) (not shown) positioned within the vasculature and having a distal tip positioned proximate or within an aneurysm. To deploy the interventional element 106, the interventional element 106 can be pushed distally (via the delivery member 108) through an opening at the distal tip of the delivery catheter and into the aneurysm cavity. Release from the constraints of the delivery catheter allows the interventional element 106 to self-expand within the aneurysm such that a portion of the interventional element 106 is positioned over the neck of the aneurysm. Once proper positioning is confirmed, the interventional element 106 can then be detached from the delivery member 108 to remain implanted within the aneurysm.

In some embodiments, the interventional element 106 may be disposed within the reservoir 114 of the packaging system 102 in a fully expanded state. In other examples, the packaging system 102 may include one or more masking and/or conductive elements (depicted schematically as element 130) that compress or otherwise confine one or more portions of the interventional element 106 to help concentrate fibrin deposition in selected areas. Additional details regarding such embodiments are discussed below with reference to FIGS. 7-10. It is noted that the relative sizing of the confined and non-confined portions of the interventional element 106 shown in FIGS. 7-10 are not necessarily to scale and are intended to communicate that a diameter of the interventional element 106 along the confined portions is less than a diameter of the interventional element 106 along the exposed portions.

As shown in FIG. 1, the interventional element 106 can be coupled to a distal end of the delivery member 108 while positioned within the reservoir 114 of the packaging system 102, and the delivery member 108 can extend through a port 150 in the wall of the reservoir 114 to a location external to the reservoir 114. In some embodiments, the medical system 100 includes an introducer sheath 110 also carried by the packaging system 102, and the delivery member 108 extends through the port 150 and into a distal end 111 of the introducer sheath 110. The introducer sheath 110 can comprise a tube and is configured to facilitate compression of the interventional element 106 into the low-profile state and transfer of the interventional element 106 and delivery member 108 into the delivery catheter for delivery to the aneurysm. For example, upon completion of the fibrin deposition onto the surface of the interventional element 106 via the charged reservoir 114, the interventional element 106 may be pulled proximally through the port 150 and into the introducer sheath 110, thereby placing the interventional element 106 in a compressed, low-profile state. In some cases, as the interventional element 106 is pulled through the port 150, a portion of the newly deposited fibrin may be sheared off the outermost surface of the interventional element 106. The inventors have observed, however, that at least in those embodiments where the interventional element 106 comprises a porous surface (e.g., a braid with pores defined between the interwoven filaments, a stent with pores defined by struts, etc.), the fibrin remains within the pores and/or on an inner surface of the interventional element 106. In some embodiments, the port 150 has an inner diameter matching the inner diameter of the introducer sheath 110, which may also match the inner diameter of the delivery catheter.

The port 150 can comprise a hemostatic valve, such as a luer lock or other coupling device that prevents blood from flowing from the reservoir 114 into the introducer sheath 110 while also allowing at least one-way passage of the interventional element 106 and delivery wire 106 therethrough. In some examples, the port 150 comprises a female connector configured to releasably mate with the distal end 111 of the introducer sheath 110 and to align the inside diameter of the introducer sheath 110 with the inside diameter of the port 150. According to some embodiments, the medical system 100 does not come with the introducer sheath 110 already attached to the reservoir 114. In some embodiments, the port 150 does not provide a fluid-tight seal around the introducer sheath 110.

Referring still to FIG. 1, the packaging system 102 can comprise a sterile barrier 103 (e.g., a bag, a flexible plastic, a container, etc.) and a tray 104 configured to be positioned within the sterile barrier 103. The tray 104 can be configured to receive and detachably secure various portions of the treatment assembly 105 and procedure-supporting devices (such as the introducer sheath 110).

As previously mentioned, a portion of the tray 104 can define a reservoir 114 in which the interventional element 106 is configured to be disposed. The reservoir 114 is also configured to receive a volume of blood therein (e.g., about 1 mL to about 60 mL, about 3 mL to about 10 mL, at least 3 mL, etc.). The reservoir 114 may be open to the environment once the sterile barrier 103 is removed, or the tray 104 can include a cover extending over and enclosing the reservoir 114. The medical system 100 can further include an injection tube 140 having one end fluidly coupled to the reservoir 114, and the other end configured to be coupled to a blood source. For example, in some embodiments a proximal portion of the injection tube 140 includes a fluid-tight connector 142 configured to be detachably coupled to a syringe or other device for transferring blood from its source to the injection tube 140. In some embodiments, the medical system 100 does not include an injection tube 140 and the connector 142 is disposed at the sidewall of the reservoir 114. In some embodiments, the medical system 100 does not include an injection tube 140 or connector 142, and blood is transferred from a syringe or other device for transferring blood from its source directly into the reservoir 114. In some embodiments, the blood for filling the reservoir is obtained from the side port of a vascular access sheath through which an interventional procedure is being performed on the patient. In such a case, the syringe may be used to collect the blood from the side port of the vascular access sheath.

As shown in FIG. 1, the packaging system 102 may further comprise a current generator 120 configured to charge the interventional element 106 when both the interventional element 106 and blood are present in the reservoir 114. The current generator 120 may comprise a power source 122 and positive and negative terminals 124, 126 electrically coupled to the power source 122. The power source 122 may be a battery integrated with the tray 104, or the tray 104 may include a cord or other wired connection for electrically coupling the positive and negative terminals 124, 126 to a wall outlet. The power source 122 can comprise a direct current power supply, an alternating current power supply, and/or a power supply switchable between a direct current and an alternating current. In some embodiments, the current generator 120 is configured to provide a current of about 1 mA to about 4 mA. The time duration of the charge can be about 30 seconds to about 5 minutes.

The negative terminal 126 of the current generator 120 can be electrically coupled via a conductive path 127 to an electrode 128 (e.g., a conductive material) disposed within the reservoir 114, while the positive terminal 126 of the current generator 120 can be electrically coupled via conductive path 125 to a portion of the interventional element 106 and/or delivery member 108. As such, activation of the current generator 120 while blood is present in the reservoir 114 applies a positive charge to the interventional element 106.

Figure 2:
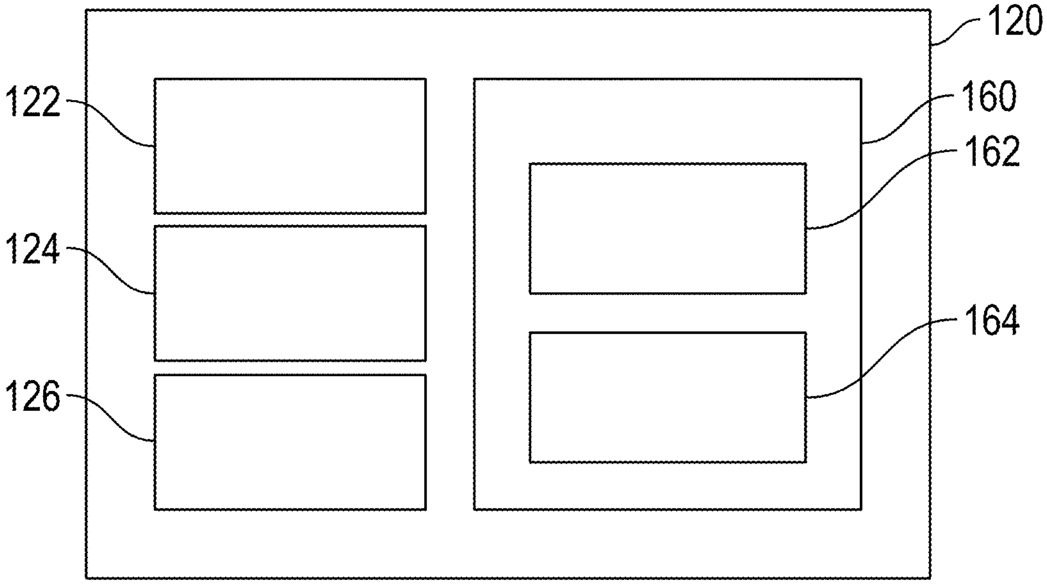
FIG. 2 schematically depicts a current generator for use with the treatment system shown in FIG. 1.
Figure 3:
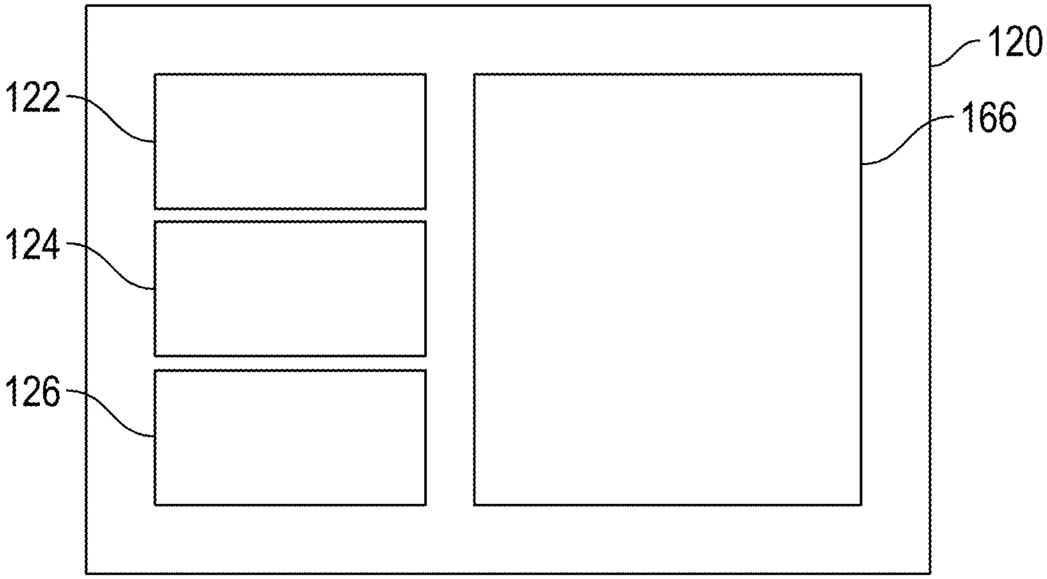
FIG. 3 schematically depicts a current generator for use with the treatment system shown in FIG. 1.

FIGS. 2 and 3 are schematic views of different embodiments of the current generator 120 configured for use with the medical systems of the present technology. With reference to FIG. 2, in some examples the current generator 120 includes a controller 160 operatively coupled to the power source 122 and positive and negative terminals 124, 126. The controller 160 includes a processor 162 coupled to a memory 164 that stores instructions (e.g., in the form of software, code or program instructions executable by the processor or controller) for causing the power source 122 to deliver electric current according to certain parameters provided by the software, code, etc. The controller 160 can be used to control various parameters of the energy output by the power source 122 or current generator 120, such as initiation of electric current delivery, intensity, amplitude, duration, frequency, duty cycle, and polarity. In some cases, the controller 160 is configured to discontinue current delivery after a predetermined amount of time corresponding to an amount of time required for sufficient fibrin accumulation (e.g., about 30 seconds to about 300 seconds). In some examples the tray 104 optionally includes an indicator 168 (e.g., a light, a speaker, a vibrational element, etc.), and the controller 160 is configured to cause the indicator 168 to provide an indication (e.g., audible, visual, tactile or any combination thereof) to the user. According to some embodiments, the tray 104 includes an input device (e.g., a button, switch, dial, etc.) (not shown) coupled to the controller 160 and configured to be manipulated by the user. In response to manipulation of the input device by the user, the controller 160 may cause the current generator 120 to turn on or off.

FIG. 3 illustrates another embodiment of the current generator 120, in which the controller of FIG. 2 is replaced with drive circuitry 166. In this embodiment, the current generator 120 can include hardwired circuit elements to provide the desired waveform delivery rather than a software-based generator of FIG. 2. The drive circuitry 166 can include, for example, analog circuit elements (e.g., resistors, diodes, switches, etc.) that are configured to cause the power source 122 to deliver electric current via the positive and negative terminals 124, 126 according to the desired parameters. For example, the drive circuitry 166 can be configured to cause the power source 122 to deliver direct current or alternating current (e.g., pulsatile, sine wave, square, triangular, and other waveforms) via the positive and negative terminals 124, 126. In some examples, delivered energy has a frequency of about 1 kHz to about 100 kHz In some embodiments, the drive circuitry 166 is configured to detect a reduction of impedance caused by the addition of blood (an electrolyte) to the reservoir 114, thereby completing the circuit and automatically beginning delivery of current to the interventional element 106.

When blood is introduced into the reservoir 114 (e.g., via the injection tube 140 and/or connector 142), and current is delivered by the current generator such that one or more portions of the interventional element 106 become positively charged, negatively charged fibrinogen is attracted to the exposed portions of the interventional element 106. Fibrinogen then converts to fibrin via a coagulation cascade, which forms a fibrous mesh on the surface of the interventional element 106, including across any pores of the interventional element 106. Without being bound by theory, the inventors believe that once the interventional element 106 is within the blood stream in the patient's body (e.g., within an aneurysm, within a parent vessel, etc.), the fibrous mesh traps platelets in the blood flowing by, and organelles within the platelets provide growth factors that promote endothelial cell proliferation, thus causing endothelialization across the surface of the interventional element 106. In short, the deposited fibrin attracts endothelial progenitors, which expedites the endothelialization process and reduces healing times.

Figure 5:
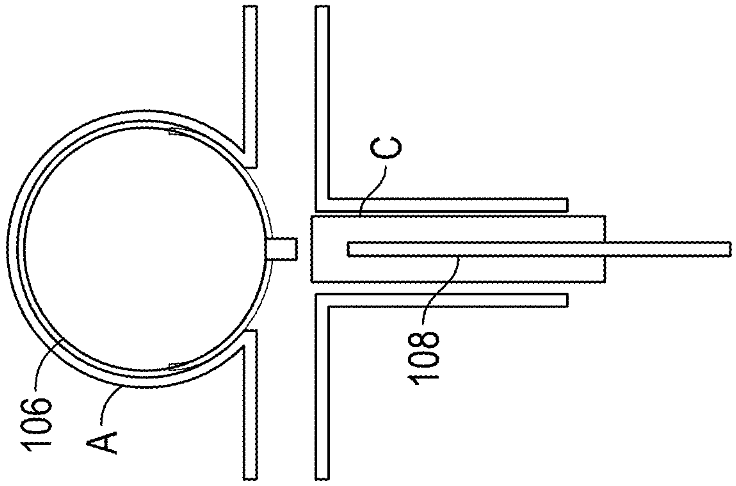
FIG. 5 shows an interventional device implanted within an aneurysm, shortly after detachment from a delivery system, in accordance with several embodiments of the present technology.
Figure 4:
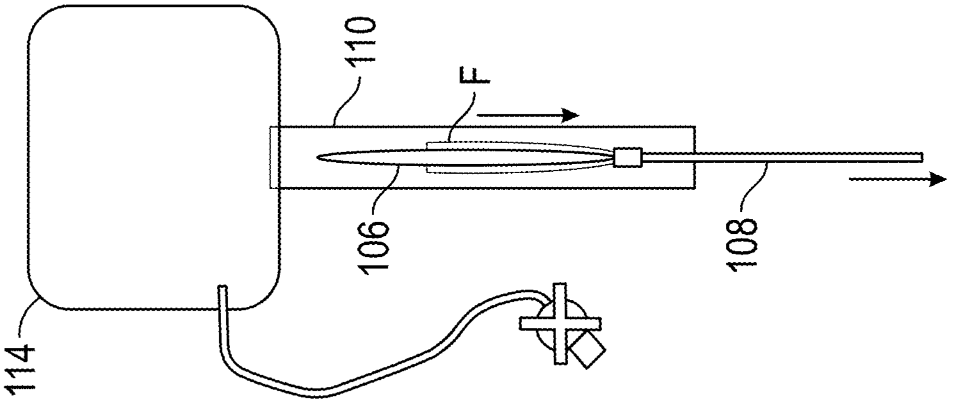
FIG. 4 shows an interventional device being removed from a reservoir of the present technology in accordance with several embodiments.

As depicted in FIG. 4, upon completion of the fibrin deposition onto the exposed surfaces of the interventional element 106 via the charged reservoir 114, the interventional element 106 may be pulled through the port 150 (e.g., via the delivery member 108) and into the introducer sheath 110. The interventional element 106 compresses down into the low-profile delivery state as it is pulled into the introducer sheath 110. Once the interventional element 106 is fully within the lumen of the introducer sheath 110, the distal end of the introducer sheath 110 can be decoupled from the port 150 and lifted from the tray 104. The distal end of the introducer sheath 110 containing the compressed interventional element 106 may then be positioned within a proximal hub of the intended delivery catheter (not shown), adjacent the proximal end of the delivery catheter lumen. The diameter of the lumen of the introducer sheath 110 (and thus the compressed diameter of the interventional element 106) can be substantially the same as the inner diameter of the delivery catheter. While holding the distal end of the introducer sheath 110 in the delivery catheter hub, adjacent the proximal end of the delivery catheter lumen, the interventional element 106 can be pushed out of the introducer sheath 110 (by pushing the delivery member 108) and into the lumen of the delivery catheter, which has typically already been positioned within the patient's vasculature. As shown schematically in FIG. 5, the interventional element 106 can then be advanced distally through the catheter C and ultimately implanted within the aneurysm A.

Figure 6:
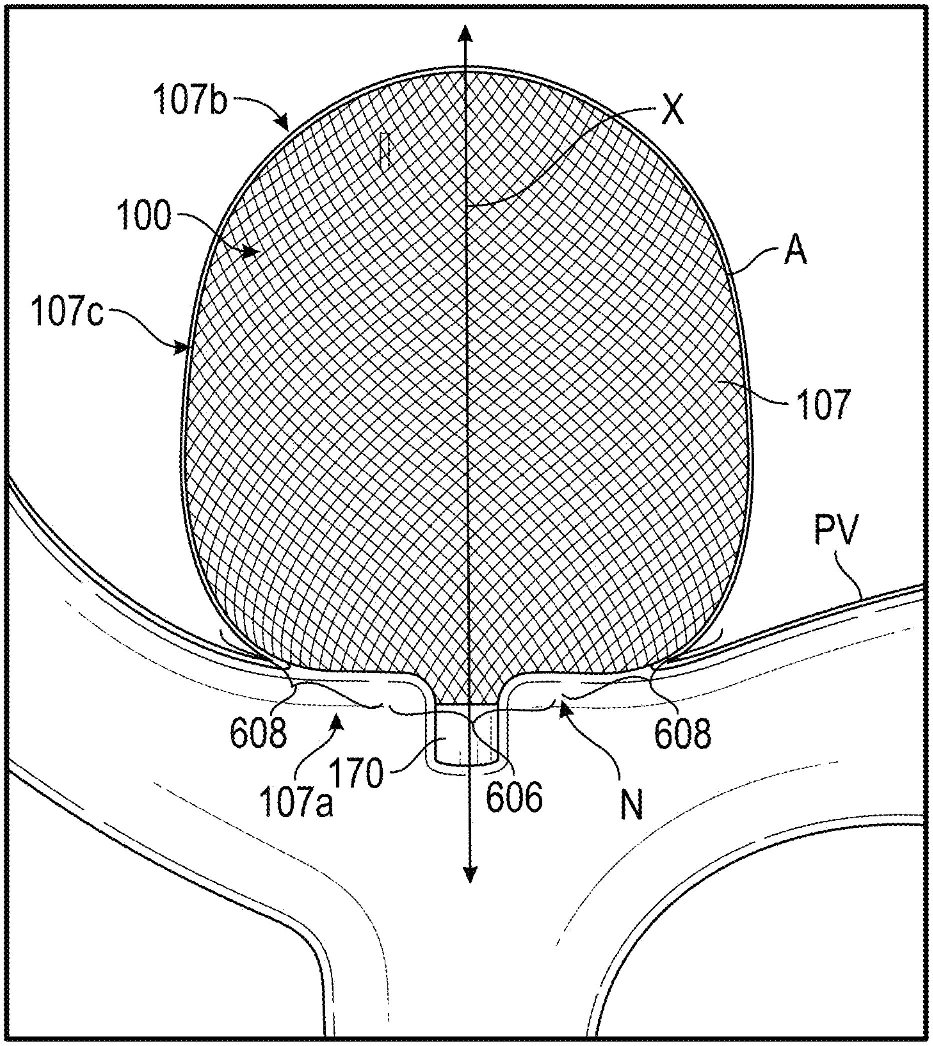
FIG. 6 shows an interventional device implanted within an aneurysm in accordance with several embodiments of the present technology.

FIG. 6 shows an example interventional element 106 positioned in an aneurysm A. The interventional element 106 comprises a mesh structure 107 formed of a plurality of braided filaments. The mesh structure 107 has a proximal region 107*a* configured to be positioned over and adjacent the neck N of the aneurysm A, a distal region 107*b* configured to be positioned near the dome of the aneurysm A, and an intermediate region 107*c* extending between the proximal and distal regions 107*a*, 107*b*. The mesh structure 107 further includes a longitudinal axis X extending between the proximal and distal regions 107*a*, 107*b*. The interventional element 106 can further include a connector 170 (e.g., a marker band) disposed at the proximal region 107*a* of the mesh structure 107, surrounding the proximal ends of the braided filaments and holding them together. In some embodiments, the connector 170 is configured to detachably couple the interventional element 106 to the delivery member 108 (not shown in FIG. 6).

The mesh structure 107 can have a compressed state for delivery within the delivery catheter to a treatment site, and an expanded state in which the mesh structure 107 is biased towards assuming a preset, three-dimensional shape. While FIG. 6 shows the mesh structure 107 forming a globular shape when in the expanded state, other shapes (e.g., a bowl, a hemisphere, a disc, an oval, etc.) are within the scope of the present disclosure.

When the mesh structure 107 is in the expanded state, the intersections of the braided filaments define a plurality of pores and the porosity of the mesh structure 107 (e.g., the percentage of a given surface area occupied by pores or voids) varies at different regions of the mesh structure 107. The proximal region 107*a* of the mesh structure 107, for example, can comprise first and second proximal regions 606, 608 having different porosities. The first proximal region 606 can immediately surround the connector 170, and the second proximal region 608 can be distal of the first proximal region 606 and/or radially outward of the first proximal region 606 but still configured to be positioned over or near the neck N. Along the first proximal region 606 the density of the filaments is relatively high (as they come together to be joined at the connector 170) and the porosity of the mesh structure 107 is relatively low. Along the second proximal region 608, the spacing between the filaments increases and the and the porosity of the mesh structure 107 is greater than that of the first proximal region 606. In some embodiments, the porosity at the first proximal region 606 is less than 5%, and in some cases 0% (e.g., non-porous), and the porosity at the second proximal region 608 is greater than 5%, or from about 5% to about 80%. In some cases, a maximum porosity of the mesh structure 107 occurs where the shoulder of the mesh structure 107 engages the neck of the aneurysm, which may be along the second proximal region 608. In these regions, the most porous would occur when the mesh structure 107 is positioned within an aneurysm having a dome/neck ratio of 1:1.

In some cases it may be desirable to deposit fibrin on select regions of the interventional element 106 to enhance occlusion in those areas. Selective deposition of fibrin may also be useful for reducing the amount of material associated with the interventional element 106, as space in catheter is limited and the presence of any additional material could make delivery of the interventional element 106 more challenging. The medical systems of the present technology can be configured to concentrate the current delivered to the interventional element 106 in select regions by masking one or more portions of the interventional element 106 and/or changing the location of where the positive current source meets the exposed portion of the interventional element 106 along the longitudinal axis X of the interventional element 106 (referred to herein as the "positive pole"). The inventors have observed that the current density is highest near the positive pole, resulting in greater fibrin deposition in the exposed regions closest to the positive pole. Additionally, lower fibrin deposition has been observed in areas of maximum pore density, and constraining the structure to reduce its pore density results in greater fibrin deposition.

One area in which fibrin deposition may be beneficial is the proximal region 107*a* of the mesh structure 107, which as previously mentioned is configured to be positioned adjacent and over the neck N. As depicted schematically in FIG. 7, in some embodiments the positive pole may be disposed at the connector 170. For example, the positive terminal 124 of the current generator 120 (see FIG. 1) can be in electrical communication with the connector 170 via the conductive path 125. In this arrangement, the proximal region 107*a* of the mesh structure 107 is closest to the positive pole and thus receives the highest current density, and also the greatest fibrin deposition. In these embodiments, the connector 170 can comprise a metal material, and in some cases a metal material with radiopaque properties.

Figure 7:
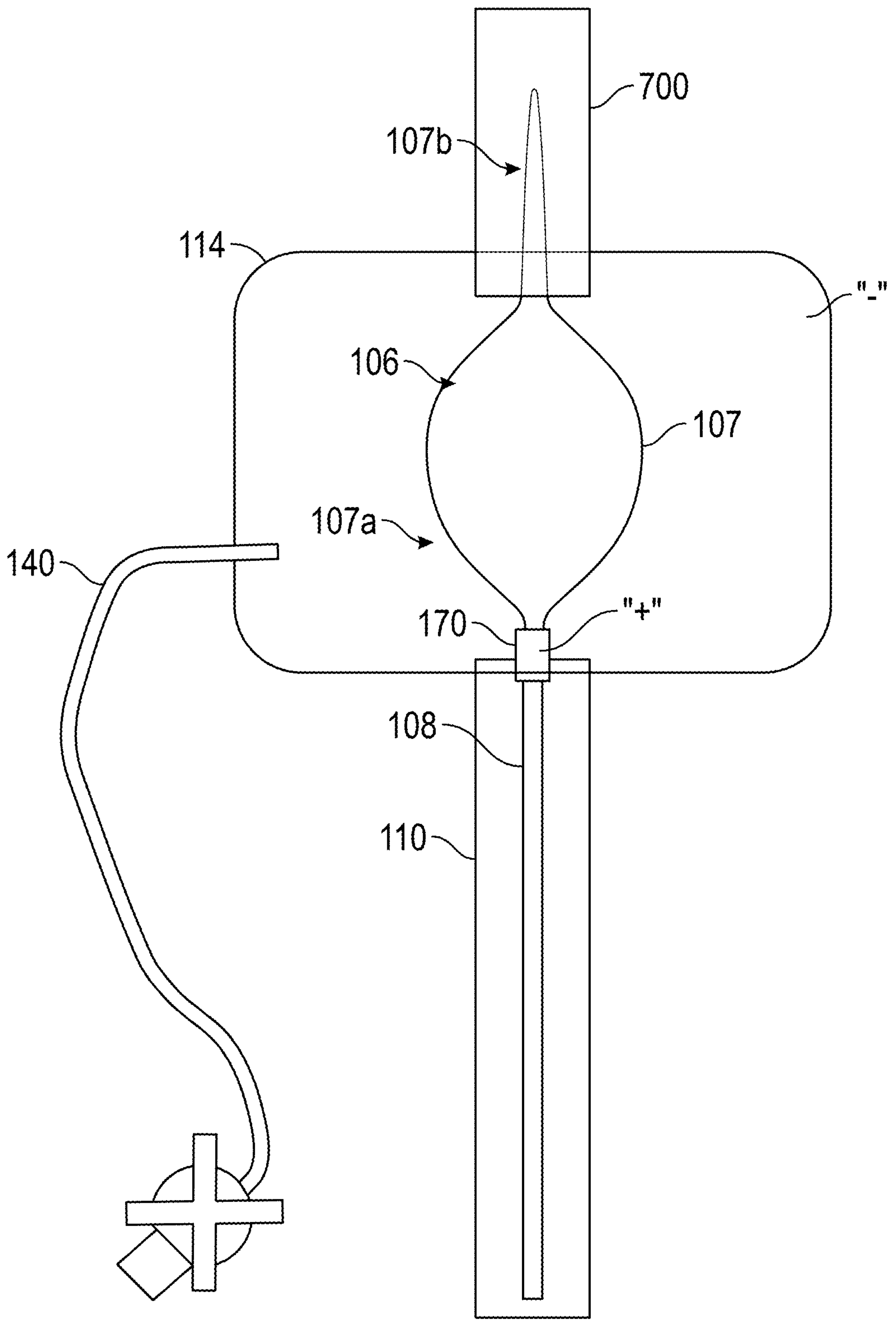
FIG. 7 schematically depicts a medical system configured in accordance with several embodiments of the present technology.

Also as depicted in FIG. 7, in some embodiments the medical system includes a mask 700 covering the distal region 107*b* of the mesh structure 107 such that the distal region 107*b* is not exposed to the blood and will not receive any fibrin deposition. While the mask 700 is shown in FIG. 7 as part of a system in which the positive pole is located at the connector 170, the mask 700 can be used with a positive pole location that is anywhere along the exposed region of the interventional element 106. In some embodiments the mask 700 comprises a channel within the tray (not shown in FIG. 7), extending from the reservoir 114, in which the distal region 107*a* has been pre-loaded during packaging. The channel can have a diameter substantially equivalent to the diameter of the mesh structure 107 in a compressed state, significantly reducing or altogether preventing contact between the masked portion of mesh structure 107 and the blood. In some examples, the mask 700 can comprise a separate tube that is positioned over the mesh structure 107 and resides partially or completely within the reservoir 114. In such cases, the tube can define a lumen having a diameter substantially equivalent to the diameter of the mesh structure 107 in a compressed state. It may be beneficial to select a length of the mesh structure 107 for positioning within the mask 700 that is sufficient to prevent the exposed portion from expanding to a degree that pulls the masked portion out of the mask 700. In any case, the unmasked portion of the mesh structure 107 is held to a small diameter, relative to fully expanded, which has the benefit of reducing the porosity of unmasked regions of the mesh structure 107 (as compared to when the mesh structure 107 is fully expanded), which increases fibrin deposition in the unmasked regions.

Figure 8:
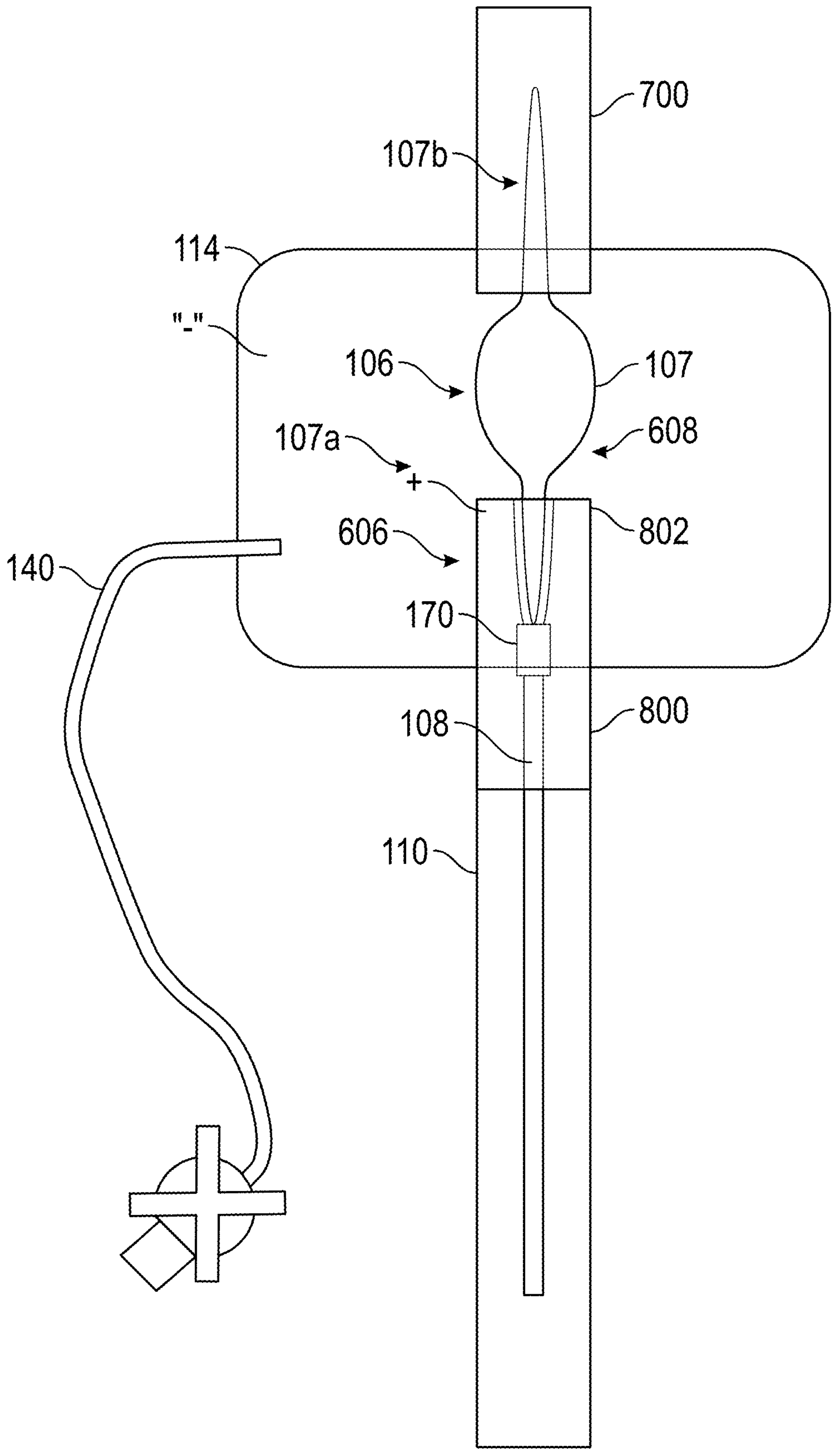
FIG. 8 schematically depicts a medical system configured in accordance with several embodiments of the present technology.

In some cases it may be desirable to locate the positive pole distal of the connector 170 and/or proximalmost portion of the mesh structure 107. While it remains true that it can be beneficial to have fibrin deposition at the proximal region 107*a* of the mesh structure 107, in some cases it may not be necessary to deposit fibrin at the region immediately surrounding the connector 170. For example, in some cases, the porosity of the first proximal region 606 is zero or close to zero and as such provides complete or substantially complete occlusion. FIG. 8 schematically depicts a portion of a medical system that includes a mask 800 disposed over the connector 170 and first proximal region 606, leaving the second proximal region 608 exposed. At least a distalmost end 802 of the mask 800 can be conductive such that the positive pole is located at the distalmost end 802, closest to the second proximal region 608 and thus concentrating the current density (and thus fibrin deposition) at the second proximal region 608. In some cases, all but the distalmost end 802 of the outer surface of the mask 800 is insulated. In some cases, all but a distal region of the outer surface of the mask 800 is insulated. In some examples, the entire mask 800 is conductive. In certain embodiments, all or a portion of the inner surface of the mask 800 may be insulated.

In some embodiments the mask 800 comprises a channel within the tray (not shown in FIG. 8), extending away from the reservoir 114, in which the first proximal region 606 has been pre-loaded during packaging. The channel can have a diameter substantially equivalent to the diameter of the mesh structure 107 in a compressed state, significantly reducing or altogether preventing the masked portion of the mesh structure 107 to contact the blood. In some examples, the mask 700 can comprise a separate tube that is positioned over the mesh structure 107 and placed within the reservoir 114 (as shown in FIG. 8). The tube may lie completely within the reservoir 114, or may extend through a sidewall of the reservoir 114 to a location in the tray beyond the reservoir 114. The tube can define a lumen having a diameter substantially equivalent to the diameter of the mesh structure 107 in a compressed state. Additionally, the mask 800 can reduce the porosity of unmasked regions of the mesh structure 107, which further results in greater fibrin deposition in unmasked regions.

While the mask 800 is shown in FIG. 8 as part of a system that also includes a mask 700 over the distal region 107*b*, the mask 800 can be used in systems without such a mask 700.

Figure 9:
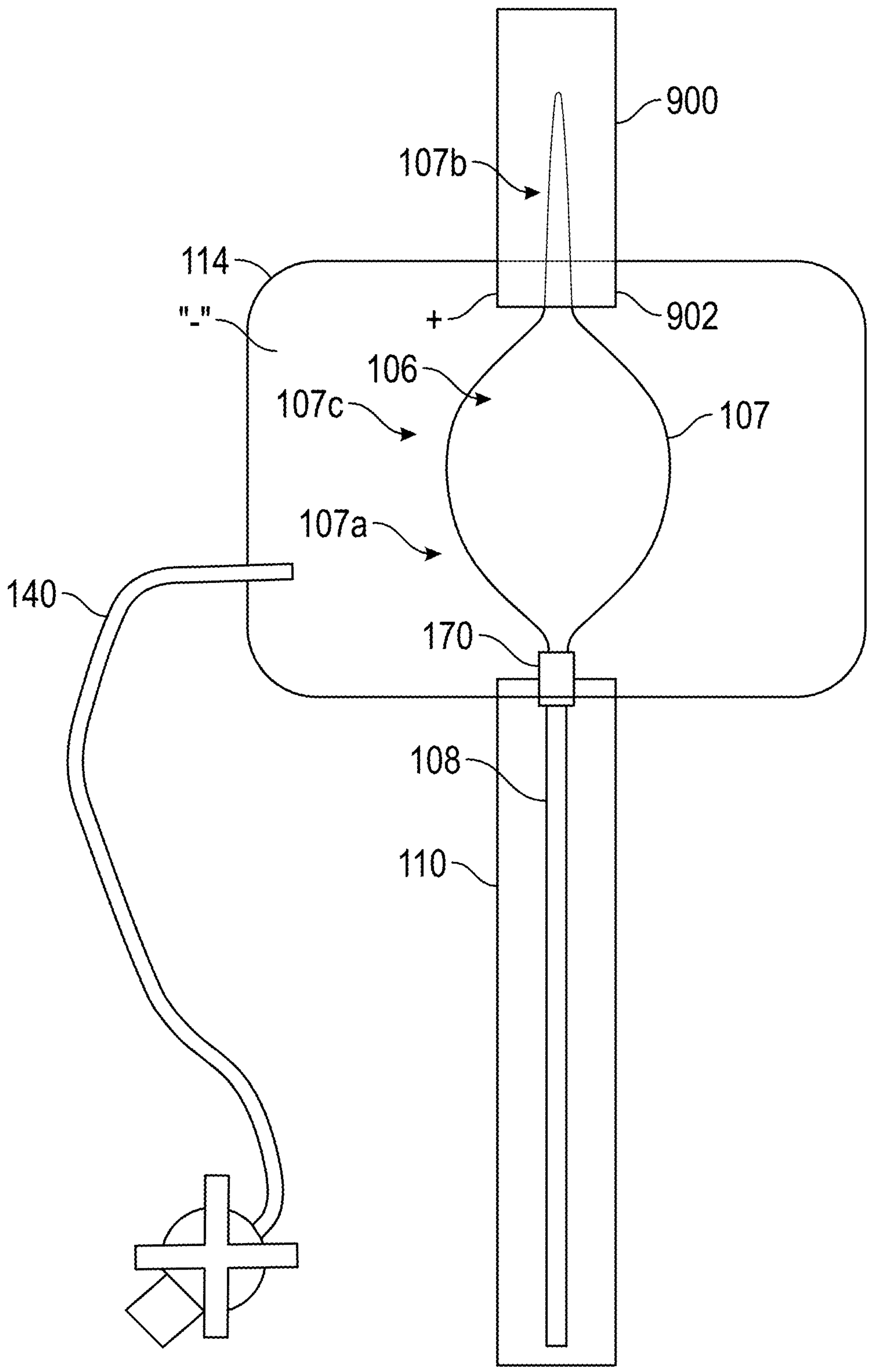
FIG. 9 schematically depicts a medical system configured in accordance with several embodiments of the present technology.

According to some aspects of the technology, it may be beneficial to focus fibrin deposition at the intermediate region 107*c* of the mesh structure 107, while still allowing some fibrin deposition at the proximal region 107*a*. Such a distribution may provide the benefit of providing an additional endothelialization accelerator inside the aneurysm sac (as the intermediate region 107*c* is configured to be positioned within the sac), in addition to at the neck. Regardless, by targeting the intermediate region 107*c* ensures the proximal region 107*a* gets coated with fibrin. FIG. 9 shows a portion of a medical system including a mask 900 disposed over the distal region 107*b*, leaving the intermediate region 107*c* and proximal region 107*a* exposed. At least a proximalmost end 902 of the mask 900 can be conductive such that the positive pole is located at the proximalmost end 902, closest to the intermediate region 107*c* and thus concentrating the current density (and thus fibrin deposition) along the intermediate region 107*c*. In some cases, all but the proximalmost end 902 of the outer surface of the mask 900 is insulated. In some cases, all but a proximal region of the outer surface of the mask 900 is insulated. In some examples, the entire mask 900 is conductive. In certain embodiments, all or a portion of the inner surface of the mask 900 may be insulated. The mask 900 can comprise a channel, tube, or other structure, as detailed above with reference to FIG. 8.

Figure 10:
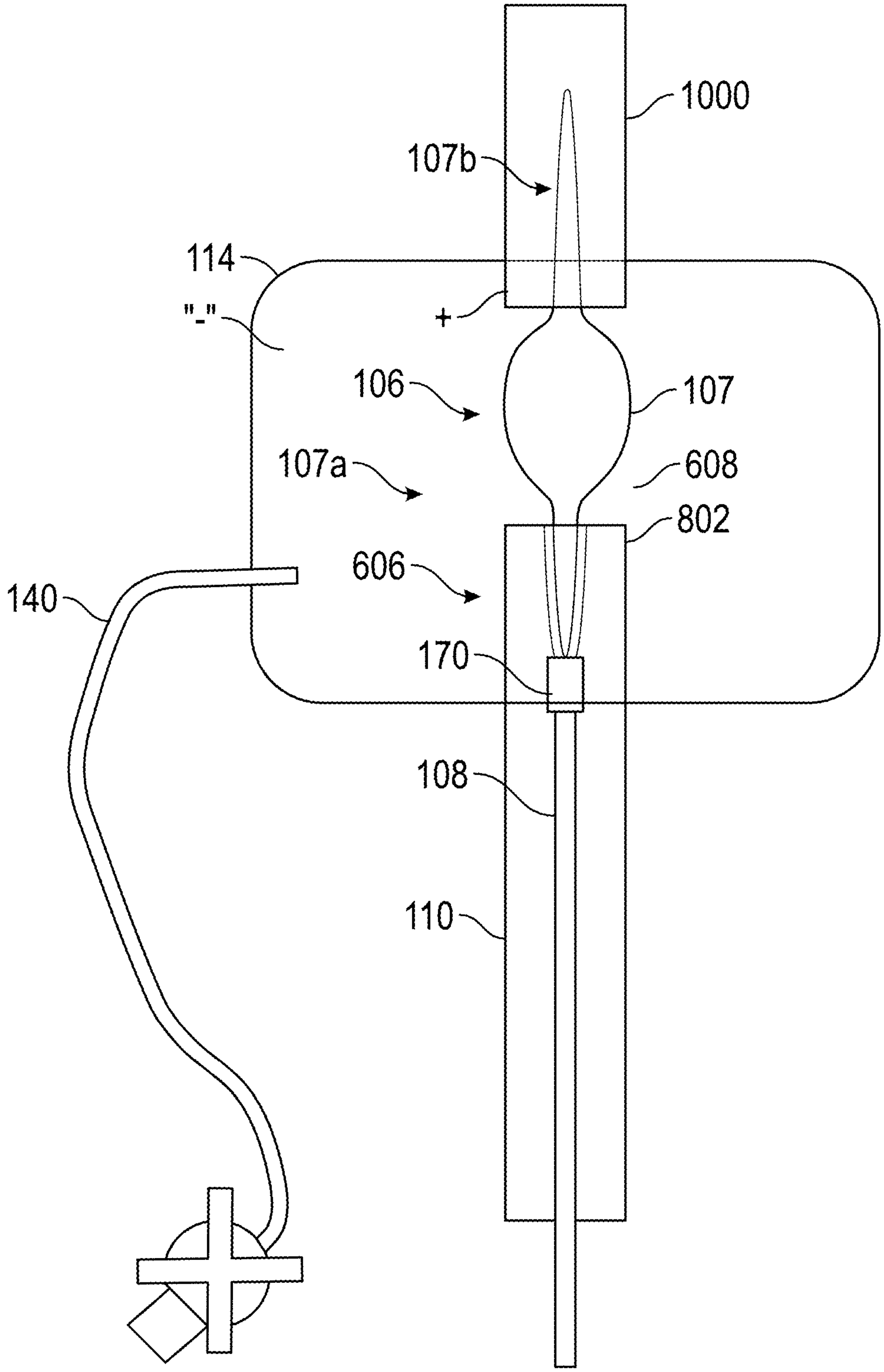
FIG. 10 schematically depicts a medical system configured in accordance with several embodiments of the present technology.

As shown in FIG. 10, in some embodiments the medical system is configured to use both conductive and non-conductive masks. For example, in some embodiments the medical system includes a conductive mask 1000 at the distal region 107*b* of the mesh structure 107, and a non-conductive mask over at least the first proximal region 606. The non-conductive mask can be the distal portion of the introducer sheath 110 (as shown in FIG. 10) or may be a separate mask. The conductive mask 1000 at the distal region 107*b* can be the same as mask 900 described above with reference to FIG. 9.

CONCLUSION

Although many of the embodiments are described above with respect to systems, devices, and methods for charging an interventional device ex vivo, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-10.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms “generally,” “substantially,” “about,” and similar terms are used as terms of approximation and not as terms of degree, and are intended to account for the inherent variations in measured or calculated values that would be recognized by those of ordinary skill in the art.

Moreover, unless the word “or” is expressly limited to mean only a single item exclusive from the other items in reference to a list of two or more items, then the use of “or” in such a list is to be interpreted as including (a) any single item in the list, (b) all of the items in the list, or (c) any combination of the items in the list. Additionally, the term “comprising” is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A medical system, comprising:

a vascular implant;

a container configured to receive and secure the vascular implant thereto, wherein a portion of the container defines a reservoir configured to receive the vascular implant and a volume of blood, and wherein the container comprises a current generator and an electrode disposed within the reservoir and configured to be electrically coupled to the generator, wherein activation of the current generator while the vascular implant and the blood are present in the reservoir causes current to flow through the blood and the vascular implant, thereby applying an electrical charge to the vascular implant.

2. The medical system of claim 1, wherein the container is a first container and the medical system further comprises a second container configured to receive the first container therein while the vascular implant is secured to the first container.

3. The medical system of claim 2, wherein the second container is a sterile barrier.

4. The medical system of claim 2, wherein the vascular implant and the first container are sterile prior to removal of the second container.

5. The medical system of claim 1, further comprising a tube extending from and in fluid communication with the reservoir, wherein the tube is configured to receive the blood therethrough and deliver the blood to the reservoir.

6. The medical system of claim 1, wherein the current generator includes a power source configured to be in electrical communication with the electrode in the reservoir.

7. The medical system of claim 1, wherein the current generator includes a negative electrical terminal and a positive electrical terminal, and wherein the negative electrical terminal is configured to be in electrical communication with the electrode.

8. The medical system of claim 1, wherein the current generator includes a negative electrical terminal and a positive electrical terminal, and wherein the positive electrical terminal is configured to be in electrical communication with the vascular implant such that upon activation of the current generator, the container applies a positive charge to the vascular implant.

9. The medical system of claim 1, further comprising an introducer sheath detachably secured to the container.

10. The medical system of claim 1, further comprising a delivery member detachably coupled to the vascular implant, wherein the container includes a port at the sidewall of the reservoir, and wherein the delivery member is configured to extend from an interior portion of the reservoir through the port to a portion of the container outside of the reservoir.

11. The medical system of claim 10, further comprising an introducer sheath having a first end detachably coupled to the port and a second end, and wherein the delivery member is configured to extend through the port and into the introducer sheath.

12. The medical system of claim 1, further comprising a mask positioned over a portion of the vascular implant, thereby reducing and/or preventing the blood in the reservoir from contacting the portion of the vascular implant.

13. The medical system of claim 12, wherein all or a portion of the mask is conductive.

14. The medical system of claim 12, wherein all of a portion of the mask is insulated.

15. A medical system, comprising:

a vascular implant;

a package defining a reservoir configured to receive the vascular implant and a volume of blood, the package including an electrode disposed within the reservoir; and a current generator configured to be electrically coupled to the electrode, wherein activation of the current generator while the vascular implant and blood are present in the reservoir causes current to flow through the blood and the vascular implant, thereby applying an electrical charge to the vascular implant.

16. A method, comprising:

positioning a vascular implant in a reservoir;

while the vascular implant is positioned in the reservoir, exposing the vascular implant to blood contained within the reservoir; and while the vascular implant is exposed to the blood, delivering an electrical current to the vascular implant, thereby depositing fibrin onto the vascular implant.

17. The method of claim 16, wherein the delivering of the electrical current comprises positively charging the vascular implant.

18. The method of claim 16, wherein all of the vascular implant is exposed to the blood during the delivery of the electrical current.

19. The method of claim 18, wherein the vascular implant is configured to be implanted within an aneurysm such that a first portion of the vascular implant is positioned over a neck of the aneurysm and a second portion of the vascular implant is configured to be positioned within an aneurysm sac.

20. The method of claim 16, wherein only a portion of the vascular implant is exposed to the blood during delivery of the electrical current.

* * * * *